(12) United States Patent
Drake et al.

(10) Patent No.: US 10,729,456 B2
(45) Date of Patent: Aug. 4, 2020

(54) SYSTEMS AND METHODS FOR DEPLOYING AN IMPLANTABLE MEDICAL ELECTRICAL LEAD

(71) Applicant: Medtronic, Inc., Minneapolis, MN (US)

(72) Inventors: Ronald A. Drake, St. Louis Park, MN (US); Kenneth C. Gardeski, Plymouth, MN (US); Zhongping Yang, Woodbury, MN (US); Rick D. McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 1110 days.

(21) Appl. No.: 14/935,708

(22) Filed: Nov. 9, 2015

(65) Prior Publication Data

US 2016/0175584 A1 Jun. 23, 2016

Related U.S. Application Data

(60) Provisional application No. 62/093,496, filed on Dec. 18, 2014.

(51) Int. Cl.
*A61B 17/32* (2006.01)
*A61B 17/34* (2006.01)
(Continued)

(52) U.S. Cl.
CPC ...... *A61B 17/32* (2013.01); *A61B 17/320016* (2013.01); *A61B 17/3468* (2013.01);
(Continued)

(58) Field of Classification Search
CPC ............ A61B 17/32; A61B 17/320016; A61B 17/3468; A61B 2017/00026;
(Continued)

(56) References Cited

U.S. PATENT DOCUMENTS 4,030,509 A 6/1977 Heilman et al.
4,146,037 A 3/1979 Flynn et al.
(Continued)

FOREIGN PATENT DOCUMENTS

CN 101072601 11/2007
EP 0517494 12/1992
(Continued)

OTHER PUBLICATIONS

Medtronic, Inc., 6996SQ Subcutaneous, Unipolar Lead with Defibrillation Coil Electrode, Technical Manual, 22 pages, 1997.
(Continued)

*Primary Examiner* — Diane D Yabut
*Assistant Examiner* — Socrates L Boutsikaris

(57) ABSTRACT

A reservoir of a system for deploying an implantable lead to an extravascular location delivers a flow of fluid through a lumen of one or both of a tunneling tool and an introducer of the system. In some cases, the tunneling tool includes a pressure sensor assembly for monitoring a change in a pressure of the flow through the lumen thereof. Alternately, or in addition, a flow-controlled passageway, through which the flow of fluid from the reservoir is delivered to the lumen of the introducer, includes a compliant chamber to hold a reserve of the fluid. Fluid from the reserve may be drawn into the lumen of the introducer as the tunneling tool is withdrawn therefrom. Alternately, the introducer may include a chamber located between two seals, wherein fluid that fills the chamber is drawn distally into the lumen of the introducer, as the tunneling tool is withdrawn therefrom.

18 Claims, 7 Drawing Sheets

(51) Int. Cl.
*A61N 1/05* (2006.01)
*A61B 17/00* (2006.01)
*A61B 90/00* (2016.01)

(52) U.S. Cl.
CPC .............. *A61B 2017/00026* (2013.01); *A61B 2017/320044* (2013.01); *A61B 2017/320056* (2013.01); *A61B 2090/064* (2016.02); *A61B 2217/007* (2013.01); *A61N 1/0504* (2013.01); *A61N 1/0563* (2013.01)

(58) Field of Classification Search
CPC ....... A61B 2017/320044; A61B 2017/320056; A61B 2217/007; A61N 1/05362; A61M 5/36; A61M 5/40
USPC ....................................... 606/129; 604/93.01
See application file for complete search history.

(56) References Cited

U.S. PATENT DOCUMENTS

| | | | |
|---|---|---|---|
| 4,270,549 A | 6/1981 | Heilman | |
| 4,280,510 A | 7/1981 | O'Neill | |
| 4,291,707 A | 9/1981 | Heilman et al. | |
| 4,437,475 A | 3/1984 | White | |
| 4,512,351 A | 4/1985 | Pohndorf | |
| 4,538,624 A | 9/1985 | Tarjan | |
| 4,552,157 A | 11/1985 | Littleford | |
| 4,664,113 A | 5/1987 | Frisbie et al. | |
| 4,765,341 A | 8/1988 | Mower et al. | |
| 4,832,687 A | 5/1989 | Smith, III | |
| 5,036,854 A | 8/1991 | Schollmeyer et al. | |
| 5,125,904 A | 6/1992 | Lee | |
| 5,176,135 A | 1/1993 | Fain et al. | |
| 5,190,529 A | 3/1993 | McCrory et al. | |
| 5,224,934 A | 7/1993 | Payne et al. | |
| 5,255,691 A | 10/1993 | Otten | |
| 5,255,692 A | 10/1993 | Neubauer et al. | |
| 5,300,106 A | 4/1994 | Dahl et al. | |
| 5,312,355 A | 5/1994 | Lee | |
| 5,441,504 A | 8/1995 | Pohndorf et al. | |
| 5,456,699 A | 10/1995 | Armstrong | |
| 5,505,707 A | 4/1996 | Manzie et al. | |
| 5,509,924 A | 4/1996 | Paspa et al. | |
| 5,613,953 A | 3/1997 | Pohndorf | |
| 5,690,648 A | 11/1997 | Fogarty et al. | |
| 5,782,239 A | 7/1998 | Webster, Jr. | |
| 5,951,518 A | 4/1999 | Licata et al. | |
| 5,944,732 A | 8/1999 | Raulerson et al. | |
| 6,032,079 A | 2/2000 | KenKnight et al. | |
| 6,104,957 A | 8/2000 | Ala et al. | |
| 6,122,552 A | 9/2000 | Tockman et al. | |
| 6,159,198 A | 12/2000 | Gardeski et al. | |
| 6,228,052 B1 | 5/2001 | Pohndorf | |
| 6,267,747 B1 | 7/2001 | Samson et al. | |
| 6,277,107 B1 | 8/2001 | Lurie et al. | |
| 6,324,414 B1 | 11/2001 | Gibbons et al. | |
| 6,415,187 B1 | 7/2002 | Kuzma et al. | |
| 6,445,954 B1 | 9/2002 | Olive et al. | |
| 6,511,434 B1 | 1/2003 | Haytman et al. | |
| 6,544,247 B1 | 4/2003 | Gardeski et al. | |
| 6,591,129 B1 | 7/2003 | Ben-Haim et al. | |
| 6,730,083 B2 | 5/2004 | Freigang et al. | |
| 6,733,500 B2 | 5/2004 | Kelley et al. | |
| 6,749,574 B2 | 6/2004 | O'Keefe | |
| 6,770,070 B1 | 8/2004 | Balbierz | |
| 6,772,014 B2 | 8/2004 | Coe et al. | |
| 6,836,687 B2 | 12/2004 | Kelley et al. | |
| 6,866,044 B2 | 3/2005 | Bardy et al. | |
| 6,887,229 B1 | 5/2005 | Kurth | |
| 6,890,295 B2 | 5/2005 | Michels et al. | |
| 6,892,087 B2 | 5/2005 | Osypka | |
| 6,921,396 B1 | 7/2005 | Wilson et al. | |
| 7,033,326 B1 | 4/2006 | Pianca et al. | |
| 7,069,083 B2 | 6/2006 | Finch et al. | |
| 7,117,039 B2 | 10/2006 | Manning et al. | |
| 7,158,838 B2 | 1/2007 | Seifert et al. | |
| 7,192,433 B2 | 3/2007 | Osypka et al. | |
| 7,195,637 B2 | 3/2007 | Mika | |
| 7,218,970 B2 | 5/2007 | Ley et al. | |
| 7,229,450 B1 | 6/2007 | Chitre et al. | |
| 7,288,096 B2 | 10/2007 | Chin | |
| 7,316,667 B2 | 1/2008 | Lindstrom et al. | |
| 7,322,960 B2 | 1/2008 | Yamamoto et al. | |
| 7,369,899 B2 | 5/2008 | Malinowski et al. | |
| 7,389,134 B1 | 6/2008 | Karicherla et al. | |
| 7,450,997 B1 | 11/2008 | Pianca et al. | |
| 7,497,844 B2 | 3/2009 | Spear et al. | |
| 7,499,758 B2 | 3/2009 | Cates et al. | |
| 7,539,542 B1 | 5/2009 | Malinowski | |
| 7,627,375 B2 | 12/2009 | Bardy et al. | |
| 7,655,014 B2 | 2/2010 | Ko et al. | |
| 7,736,330 B2 | 6/2010 | Bardy | |
| 7,765,014 B2 | 7/2010 | Eversull et al. | |
| 7,801,622 B2 | 9/2010 | Camps et al. | |
| 7,815,604 B2 | 10/2010 | Massengale et al. | |
| 7,837,671 B2 | 11/2010 | Eversull et al. | |
| 7,846,088 B2 | 12/2010 | Ness | |
| 7,850,610 B2 | 12/2010 | Ferek-Petric | |
| 7,930,040 B1 | 4/2011 | Kelsch et al. | |
| 7,983,765 B1 | 7/2011 | Doan et al. | |
| 8,060,207 B2 | 11/2011 | Wallace et al. | |
| 8,065,020 B2 | 11/2011 | Ley et al. | |
| 8,066,702 B2 | 11/2011 | Rittman, III et al. | |
| 8,083,728 B2 | 12/2011 | Rome | |
| 8,090,451 B2 | 1/2012 | Tyson, Jr. | |
| 8,155,755 B2 | 4/2012 | Flynn et al. | |
| 8,157,813 B2 | 4/2012 | Ko et al. | |
| 8,260,436 B2 | 9/2012 | Gerber et al. | |
| 8,280,527 B2 | 10/2012 | Eckerdal et al. | |
| 8,328,738 B2 | 12/2012 | Frankhouser et al. | |
| 8,340,779 B2 | 12/2012 | Harris et al. | |
| 8,355,786 B2 | 1/2013 | Malinowski | |
| 8,386,052 B2 | 2/2013 | Harris et al. | |
| 8,394,079 B2 | 3/2013 | Drake et al. | |
| 8,435,208 B2 | 5/2013 | Bardy | |
| 8,442,620 B2 | 5/2013 | Silipo et al. | |
| 8,452,421 B2 | 5/2013 | Thenuwara et al. | |
| 8,478,424 B2 | 7/2013 | Tronnes | |
| 8,478,426 B2 | 7/2013 | Barker | |
| 8,886,311 B2 | 11/2014 | Anderson et al. | |
| 2002/0120294 A1 | 8/2002 | Kroll | |
| 2003/0114908 A1 | 6/2003 | Flach | |
| 2004/0030333 A1 | 2/2004 | Goble | |
| 2004/0059348 A1 | 3/2004 | Geske et al. | |
| 2004/0102829 A1 | 5/2004 | Bonner et al. | |
| 2004/0210293 A1 | 10/2004 | Bardy et al. | |
| 2004/0236396 A1 | 11/2004 | Coe et al. | |
| 2005/0049663 A1 | 3/2005 | Harris et al. | |
| 2005/0131505 A1 | 6/2005 | Yokoyama | |
| 2005/0288758 A1 | 12/2005 | Jones et al. | |
| 2005/0288759 A1* | 12/2005 | Jones ................ A61B 17/3415 607/116 |
| 2006/0041295 A1 | 2/2006 | Okypka | |
| 2006/0116746 A1 | 6/2006 | Chin | |
| 2006/0122676 A1 | 6/2006 | Ko et al. | |
| 2006/0253181 A1 | 11/2006 | Schulman et al. | |
| 2007/0023947 A1 | 2/2007 | Ludwig et al. | |
| 2007/0055204 A1 | 3/2007 | Geisler et al. | |
| 2007/0100409 A1 | 5/2007 | Worley et al. | |
| 2007/0173900 A1 | 7/2007 | Siegel et al. | |
| 2007/0179388 A1 | 8/2007 | Larik et al. | |
| 2007/0191781 A1* | 8/2007 | Richards .......... A61B 17/00491 604/191 |
| 2007/0208402 A1 | 9/2007 | Helland et al. | |
| 2007/0249992 A1 | 10/2007 | Bardy | |
| 2008/0046056 A1 | 2/2008 | O'Connor | |
| 2008/0243219 A1 | 10/2008 | Malinowski et al. | |
| 2008/0249501 A1 | 10/2008 | Yamasaki | |
| 2008/0269716 A1 | 10/2008 | Bonde et al. | |
| 2008/0269763 A1 | 10/2008 | Bonde et al. | |
| 2009/0076476 A1 | 3/2009 | Barbagli et al. | |
| 2009/0157091 A1 | 6/2009 | Buysman | |
| 2009/0222021 A1 | 9/2009 | Chang et al. | |

(56) References Cited

U.S. PATENT DOCUMENTS

| | | |
|---|---|---|
| 2009/0259283 A1 | 10/2009 | Brandl et al. |
| 2009/0264780 A1 | 10/2009 | Schilling |
| 2010/0010442 A1* | 1/2010 | Shivkumar ........... A61M 5/385 604/122 |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0179562 A1 | 7/2010 | Linker et al. |
| 2010/0217298 A1 | 8/2010 | Bardy et al. |
| 2010/0217301 A1 | 8/2010 | Bardy et al. |
| 2010/0249696 A1 | 9/2010 | Bardy et al. |
| 2010/0262158 A1 | 10/2010 | Siegel et al. |
| 2010/0305428 A1 | 12/2010 | Bonner et al. |
| 2010/0318098 A1 | 12/2010 | Lund et al. |
| 2011/0009933 A1 | 1/2011 | Barker et al. |
| 2011/0224680 A1 | 9/2011 | Barker et al. |
| 2011/0224681 A1 | 9/2011 | McDonald |
| 2011/0230906 A1 | 9/2011 | Modesitt et al. |
| 2011/0257660 A1 | 10/2011 | Jones et al. |
| 2012/0016377 A1 | 1/2012 | Geroy |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu et al. |
| 2012/0209285 A1 | 8/2012 | Barker et al. |
| 2012/0215218 A1 | 8/2012 | Lipani |
| 2012/0220894 A1 | 8/2012 | Melsheimer |
| 2013/0066331 A1 | 3/2013 | Chitre et al. |
| 2013/0103049 A1 | 4/2013 | Bonde |
| 2013/0158564 A1 | 6/2013 | Harris et al. |
| 2013/0238067 A1 | 9/2013 | Baudino et al. |
| 2014/0330248 A1* | 11/2014 | Thompson-Nauman ..................... A61N 1/05 604/506 |

FOREIGN PATENT DOCUMENTS

| | | |
|---|---|---|
| EP | 1634615 | 3/2006 |
| WO | 2001023035 A1 | 4/2001 |
| WO | 2004073506 A2 | 9/2004 |
| WO | 2012/159000 A2 | 11/2012 |

OTHER PUBLICATIONS

Medtronic, Inc., 6996T Tunneling Tool, Technical Manual, 12 pages. 1997.

Greatbatch Medical, OptiSeal Valved Peelable Introducer Brochure, 2 pages, 2010.

Appeal Brief from U.S. Appl. No. 14/257,519, dated Oct. 17, 2019, 22 pp.

Haydin et al., "Subxiphoid Approach to Epicardial Implantation of Implantable Cardioverter Defibrillators in Children", Pace, vol. 36, Aug. 2013, 6 pp.

Avogadros Lab Supply Inc., Catalog; Scoopula with Beech Wood Handle, can be found on-line at http://www.avogadro-lab-supply.com/search.php, accessed Feb. 18, 2014, 1 page.

Baudoin et al., "The Superior Epigastric Artery Does Not Pass Through Larrey's Space (Trigonum Sternocostale)," Surg Radiol Anat, vol. 25, Aug. 1, 2003, 4 pp.

Bielefeld et al., "Thoracoscopic Placement of Implantable Cardioverter-Defibrillator Patch Leads in Sheep", Circulation, vol. 88, Park 2, Nov. 1993, 5 pp.

Bolling et al., "Automatic Internal Cardioverter Defibrillator: A Bridge to Heart Transplantation", Heart Lung Transplantation, Abstract Only, Jul.-Aug. 1991, 1 page.

Cigna et al., "A New Technique for Substernal Colon Transposition with a Breast Dissector: Report of 39 Cases" Elsevier, JPRAS, An International Journal of Surgical Reconstruction, Journal of Plastic, Reconstructive & Aesthetic Surgery, vol. 59, Sep. 24, 2005, 4 pp.

Damiano, "Implantation of Cardioverter Defibrillators in the Post -Sternotomy Patient", The Annals of Thoracic Surgery, vol. 53, Presented at the Thirty-eighth Annual Meeting of the Southern Thoracic Surgical Association, Nov. 7-9, 1992, pp. 978-983.

Ely et al., "Thoracoscopic Implantation of the Implantable Cardioverter Defibrillator", Minimally Invasive Techniques, Chest, vol. 103, Issue 1, (Can be found on the World-Wide Web at http://chestioumal.chestpubs.org on May 6, 2013), dated Jan. 1993; 2 pp.

Frame et al., "Long-Term Stability of Defibrillation Thresholds with Intrapericardial Defibrillator Patches", Deparments of Cardiothoracic Surgery and medicine, Montefiore Medical Center, Pace, vol. 16, Jan. 1993, 6 pp.

Ganapathy et al., "Implantable Device to Monitor Cardiac Activity with Sternal Wires," Pace—Pacing and Clinical Electrophysiology, Official Journal of the World Society of Arhythmias, vol. 37, Issue 12, Dec. 2014, 11 pp.

Guenther et al., "Substernal Lead Implantation: A Novel Option to Manage OFT Failure in S-ICD patients," Springer, Clinical Research Cardiology, vol. 104, Oct. 2, 2014, 3 pp.

Harman et al., "Differences in the Pathological Changes in Dogs' Hearts After Defibrillation with Extrapericardial Paddles and Implanted Defibrillator Electrodes", Journal of Pacing and Clinical Electrophysiology, Pace, vol. 14, Part 2, Feb. 1991, 5 pp.

Karwande et al.,"Bilateral Anterior Thoracotomy for Automatic Implantable Cardioverter Defibrillator Placement in Patients with Previous Sternotomy," The Society of Thoracic Surgeons, The Annals of Thoracic Surgery, vol. 54, Oct. 1992, 3 pp.

Lawrie et al., "Right Mini-Thoracotomy: An Adjunct to Left Subcostal Automatic Implantable Cardioverter Defibrillator Implantation," The Society of Thoracic Surgeons, The Annals of Thoracic Surgery, vol. 47, Nov. 18, 1989, 4 pp.

Lemmer, "Defibrillator Patch Constriction, Letter to the Editor," The Annals of Thoracic Surgery, vol. 61, Applicant points out, in accordance with MPEP 609.04(a), that the year of publication, 1996, is sufficiently earlier than the effective U.S. filed, so that the particular month of publication is not in issue.), 1 pp.

Mitchell et al., "Experience with an Implantable Tiered Therapy Device Incorporating Antitachycardia Pacing and Cardioverter/Defibrillator Therapy," Thoracic and Cardiovascular Surgery, Abstract Only, Mar. 1993, 1 pp.

Molina et al, "An Epicardial Subxiphoid Implantable Defibrillator Lead: Superior Effectiveness After Failure of Standard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pp.

Obadia et al., "Thoracoscopic Approach to Implantable Cardioverter Defibrillator Patch Electrode Implantation," Pace, Pacing and Clinical Electrophysiology, vol. 19, Jun. 1996, 6 pp.

Obadia et al., "New Approach for Implantation of Automatic Defibrillators Using Videothoracoscopy," Journal Ann Cardiol Angeiol (Paris), vol. 43, Issue 7, Sep. 1994, Abstract Only, 1 pp.

Pebax Product Brochure, 14 pages and can be found on-line at http://www.pebax.com/export/sites/pebax/content/medias/downloads/literature/pebax-product-rang-brouchure.pdf, accessed on Feb. 28, 2014, 14 pp.

Piccione, et al. "Erosion of ExtrapericardialImplantable Cardioverter Defibrillator Patch Through the Gastic Fundus with Fistulous Tract Information", Cardiology in Review, vol. 14, No. 6, Nov./Dec. 2006, 3 pp.

Quigley et al., "Migration of an Automatic Implantable Cardioverter-Defibrillator Patch Causing Massive Hemothorax", Journal Texas Heart Institute, vol. 23, Nov. 1, 1996, 4 pages.

Shapira et al., A Simplified Method for Implantation of Automatic Cardioverter Defibrillator in Patients with Previous Cardiac Surgery, Pace, Pacing and Clinical Electrophysiology, vol. 16, Part 1, Jan. 1993, 6 pp.

(56) References Cited

OTHER PUBLICATIONS

Steinke et al., Subepicardial Infarction, Myocardial Impression, and Ventricular Penetration by Sutureless Electrode and Leads, Chest, vol. 70, Issue 1, Jul. 1976, 2 pp.

Substernal Medical Definition, Copyright 2019 Merriam-Webster, Incorporated, accessed fromhttps://www.merriam-webster.com/medical/substernal, accessed on Oct. 3, 2019, 1 pp.

Tung et al., "Initial Experience of Minimal Invasive Extra Cardiac Placement of High Voltage Defibrillator Leads," Canadian Cardiovascular Congress 2007, vol. 23, Oct. 2007, 4 pp.

Tung et al., "Minimal Invasive Extra Cardiac Placement of High Voltage Defibrillator Leads", Poster 3; S200 Abstract, P0-3-4; St. Paul Hospital, Vancouver, British Columbia, Canada, Accessed on Aug. 12, 2014, 1 pp.

Vyhmeister et al., "Simple Approach for Extrapericardial Placement of Defibrillator Patches via Median Sternotomy," The Society of Thoracic Surgeons, The Annals of Thoracic Surgery, vol. 57, Dec. 4, 1994, 4 pp.

Prosecution History from U.S. Appl. No. 14/257,519, dated Dec. 4, 2015 through Aug. 19, 2019, 177 pp.

Office Action from U.S. Appl. No. 14/257,519, dated Feb. 6, 2020, 16 pp.

Response to Office Action dated Feb. 6, 2020, from U.S. Appl. No. 14/257,519, filed May 4, 2020, 9 pp.

\* cited by examiner

SYSTEMS AND METHODS FOR DEPLOYING AN IMPLANTABLE MEDICAL ELECTRICAL LEAD

CROSS-REFERENCE TO RELATED APPLICATION

The instant application claims priority to the United States Provisional Application of the same title and having the Ser. No. 62/093,496, which was filed on Dec. 18, 2014, and which is hereby incorporated by reference in its entirety.

TECHNICAL FIELD

The present disclosure is related to implantable medical electrical leads, and more particularly pertains to systems and methods for the deployment thereof.

BACKGROUND

Implantable cardiac defibrillator (ICD) systems are used to delivery high energy electrical pulses or shocks to a patient's heart to terminate life-threatening arrhythmias, such as ventricular fibrillation. Traditional ICD systems include an ICD device and one or more implantable medical electrical leads connected thereto; the device, which has a hermitically sealed housing that encloses a pulse generator and other electronics thereof, is implanted subcutaneously in the chest of the patient, and the leads, referred to herein as transvenous leads, are implanted within the heart.

Traditional ICD systems that utilize transvenous leads may not be preferred for all patients, such as those in whom difficult vascular access precludes the placement of transvenous leads. Moreover, transvenous leads may become fibrosed in the heart over time, making lead revision and extraction procedures challenging. Thus, for some patients, an extravascular ICD system may be preferred, in which a lead (or leads) are implanted in an extravascular location, that is, outside the vascular system of the patient, rather than within the vascular system, for example, in a subcutaneous, sub-sternal, or other extravascular location.

SUMMARY

Embodiments and methods of the present invention, which are disclosed herein, address some difficulties caused when creating tunnels in extravascular locations, for example, within a subcutaneous or sub-sternal space, to which medical electrical leads are deployed for implant. Some specific difficulties are described below, in the Detailed Description section.

According to some embodiments, a tunneling tool of a system for deploying an implantable medical electrical lead to an extravascular location, for example, a sub-sternal space in a body of a patient, has a lumen extending along a length of a shaft of the tool and a pressure sensor assembly mounted in a handle of the tool. The system further includes a fluid supply assembly with a flow-controlled passageway, which, when coupled to a port of the tunneling tool handle, delivers a flow of fluid through the tunneling tool lumen, for example, while an operator employs the tool to create a tunnel within the aforementioned space. According to some methods of the present invention, the operator can monitor, via a display of the pressure sensor assembly, a change in a pressure of the flow, as measured by a pressure transducer of the pressure sensor assembly.

Alternately, or in addition, the fluid supply assembly of some embodiments of the present invention includes a flow-controlled passageway having a compliant chamber, which may be coupled to a port of an introducer to deliver flow of fluid through a lumen of the introducer which is snuggly fitted around a shaft of a tunneling tool, either a standard tunneling tool or one like that described above. According to some methods, the flow-controlled passageway is filled with fluid and the compliant chamber located at an elevation lower than that of the tunnel created by the tunneling tool, so that when the operator withdraws the shaft of the tunneling tool from the lumen of the introducer, after creating the tunnel within the sub-sternal space, fluid from a reserve of fluid filling the compliant chamber is drawn into the lumen of the introducer.

According to some additional embodiments, an introducer of a system for deploying an implantable medical electrical lead to an extravascular location, for example, a sub-sternal space in a body of a patient, has a hub that includes a distal seal and a proximal seal; and a lumen of the introducer, which extends from a proximal opening thereof, formed by the proximal seal, to a distal opening thereof, at a tapered distal end of a tubular member of the introducer, includes a chamber located between the seals of the hub. The introducer hub further includes first, second, and third ports, each of which is in fluid communication with the chamber, wherein the third port is configured to accommodate a standing column of fluid from the chamber, for example, being supplied from a flow-controlled passageway of a fluid supply assembly of the system that is coupled to the second port of the introducer hub to fill the chamber with fluid. The lumen of the introducer may be snuggly fitted around a shaft of a tunneling tool; and, as the tunneling tool shaft is withdrawn out through the proximal opening of the lumen, fluid that fills the chamber of the introducer hub is drawn distally through the distal seal of the introducer hub and into the lumen that extends within the tubular member.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1A:
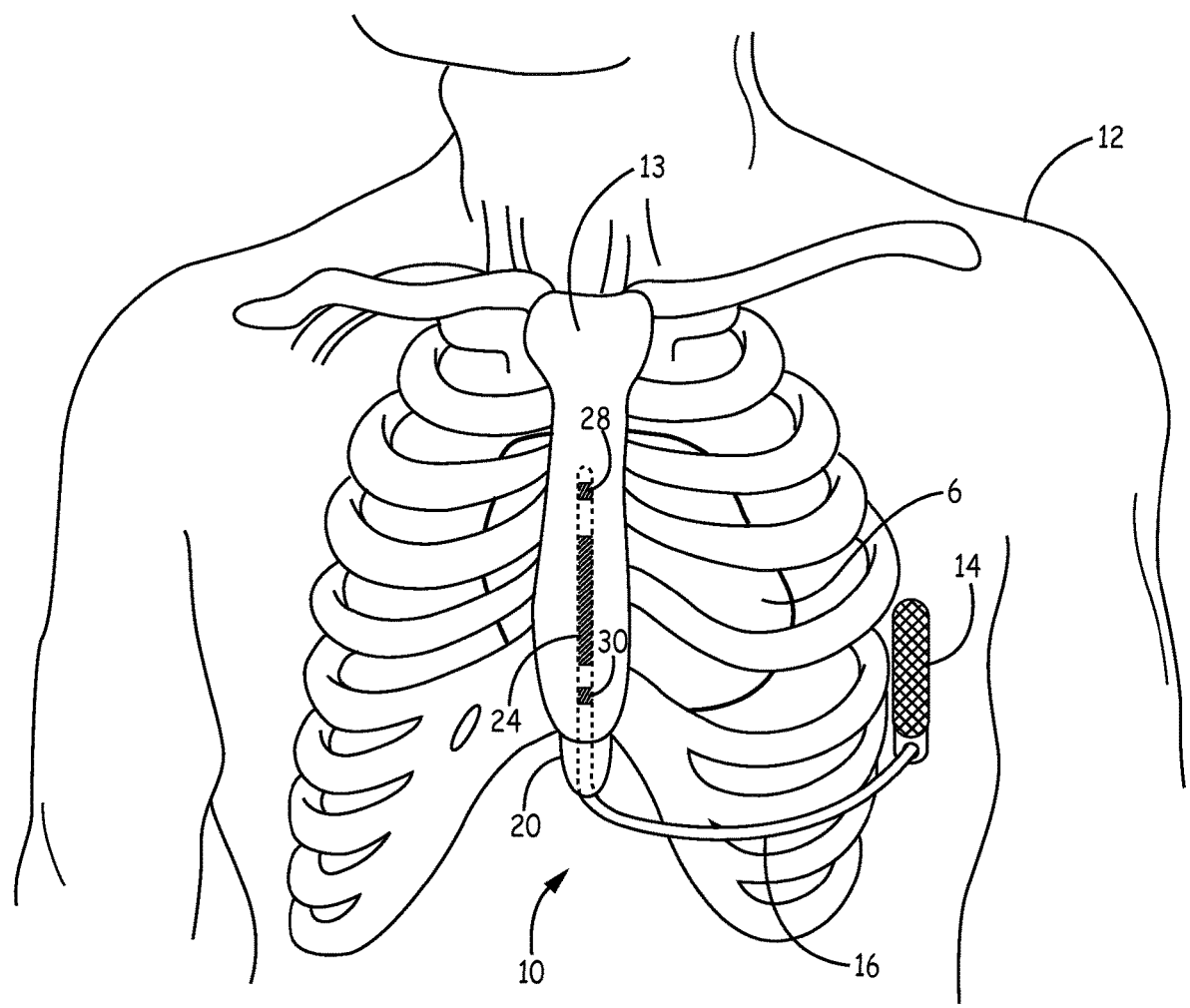
FIG. 1A is a front view of an exemplary extravascular ICD system implanted within a patient.
Figure 1B:
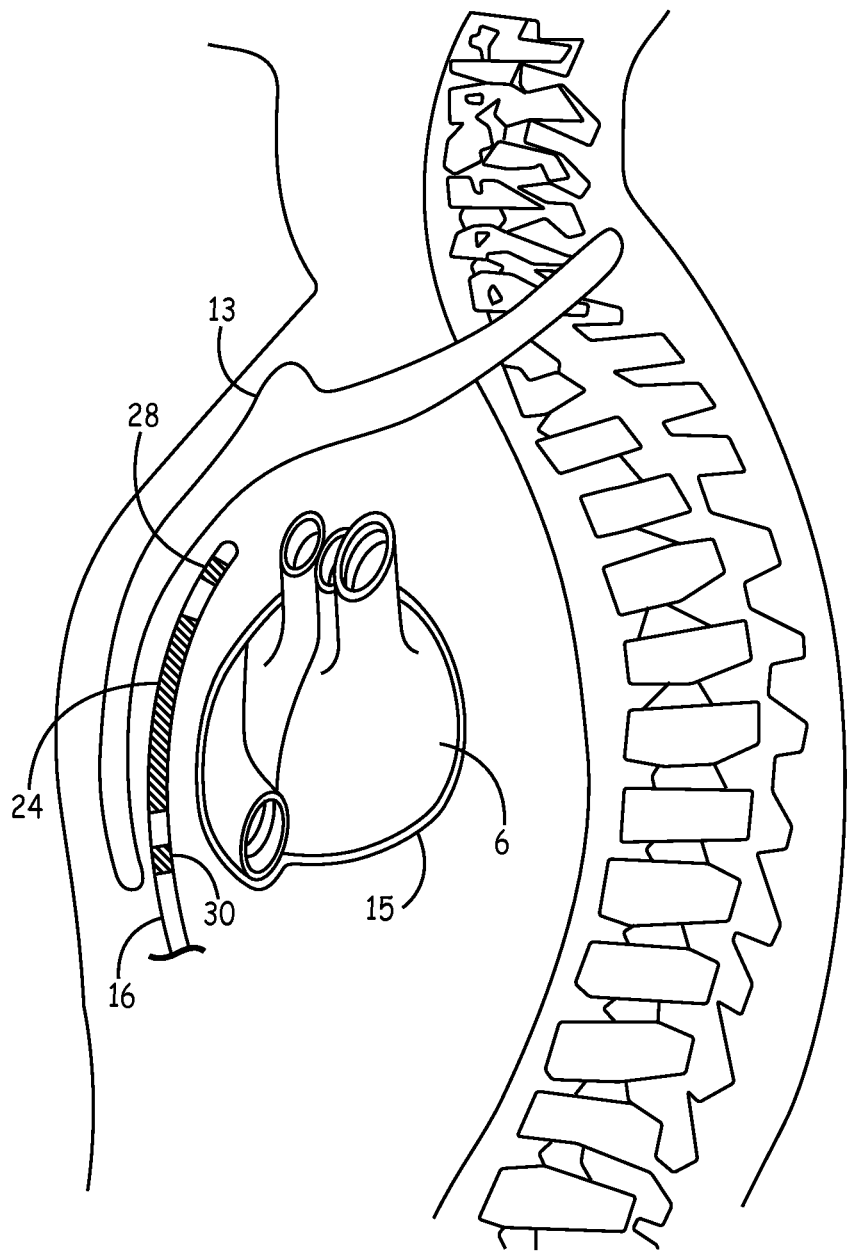
FIG. 1B is a side view of the implanted ICD system.
Figure 1C:
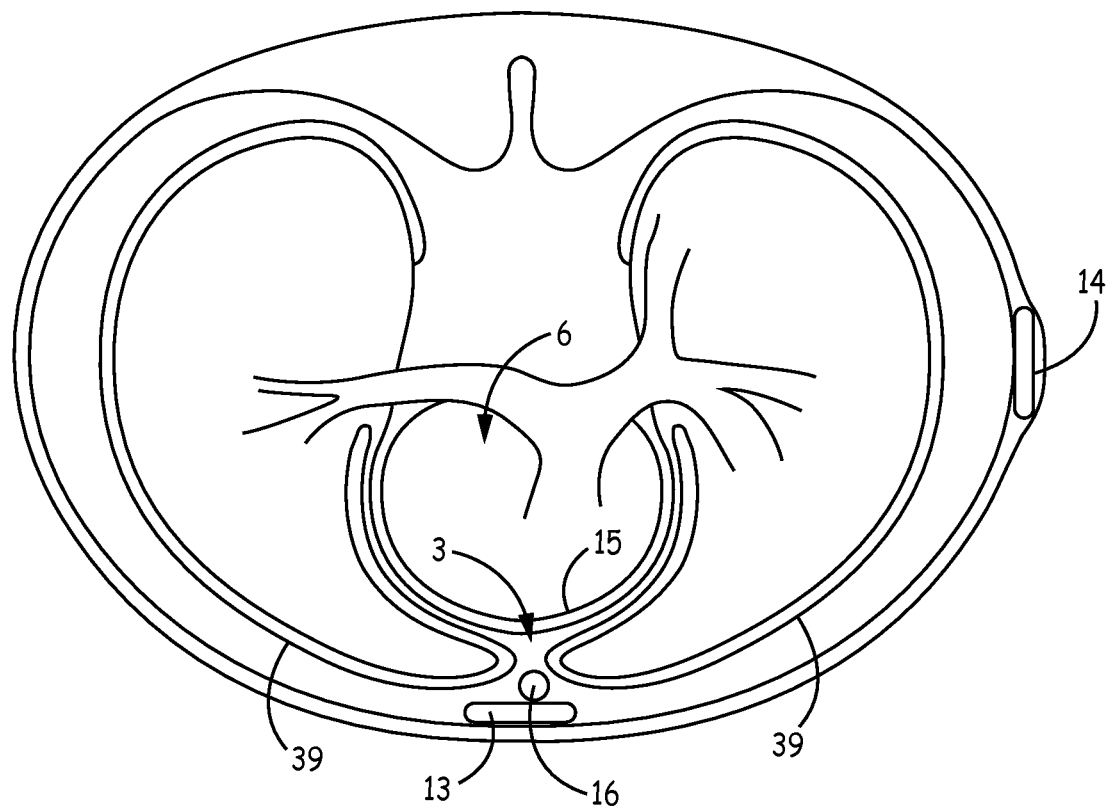
FIG. 1C is a transverse view of the implanted ICD system.

FIGS. 1A-C are conceptual diagrams of an exemplary extravascular ICD system 10 implanted within a patient 12. Although FIGS. 1A-C are described in the context of cardioversion and cardiac defibrillation therapy, systems and methods for deploying an implantable medical electrical lead, according to the instant disclosure, may be employed for implantable medical devices configured to provide other types of cardiac therapy. FIG. 1A illustrates system 10 including an implantable ICD device 14 and an implantable medical electrical lead 16, which is coupled thereto, wherein ICD device 14 is shown implanted subcutaneously on the left mid-axillary of patient 12, superficially of the patient's ribcage. ICD device 14 includes a hermetically sealed housing in which a pulse generator and other electronics are contained, and which may be formed from a conductive material, such as titanium, or from a combination of conductive and non-conductive materials, wherein the conductive material of housing may be employed as an electrode, for example, to provide cardiac defibrillation therapy in conjunction with a defibrillation electrode 24 of lead 16. ICD device may also include a connector header attached to the housing by which lead 16 is electrically coupled to the electronics contained therein, for example, by electrical contacts contained within the header and a corresponding hermetically sealed feedthrough assembly, such as is known in the art.

FIGS. 1A-B further illustrate lead 16 including an elongate body extending from a proximal connector assembly, which is coupled to the aforementioned connector header of ICD device 14 to a distal portion, about which electrodes 24, 28 and 30 are mounted, wherein each electrode 24, 28, 30 is coupled to a corresponding connector of the connector assembly by an elongate conductor extending within the body of lead 16. Lead 16 extends subcutaneously from ICD device 14, superficial to the ribcage, and toward a center of the torso of patient 12. At a location near the center of the torso, e.g., in proximity to a xiphoid process 20 of the patient's sternum 13, lead 16 bends or turns in a superior direction, and extends under/below sternum 13 within the patient's anterior mediastinum 3, which is best seen in FIG. 1C, so that electrodes 24, 28, 30 are located in proximity to the patient's heart 6.

With reference to FIG. 1C, the anterior mediastinum 3 may be viewed as being bounded laterally by pleurae 39 that enclose the patient's lungs, posteriorly by pericardium 15 that encloses the patient's heart 6, and anteriorly by the sternum 13. In some instances, the anterior wall of the anterior mediastinum 3 may also be formed by the transversus thoracis and one or more costal cartilages. The anterior mediastinum 3 includes a quantity of loose connective tissue (such as areolar tissue), some lymph vessels, lymph glands, sub-sternal musculature (e.g., transverse thoracic muscle), branches of the internal thoracic artery, and the internal thoracic vein. In one example, the distal portion of lead 16 may be implanted substantially within the loose connective tissue and/or sub-sternal musculature of the anterior mediastinum 3. Systems and methods described herein may be used to deploy lead 16 to this extravascular location, however, according to alternate embodiments, the distal portion of lead 16 may be implanted in other non-vascular, extra-pericardial locations, for example, anywhere within a sub-sternal space defined by the undersurface of the sternum 13 and/or ribcage and the pericardium or other portion of heart 6. The sub-sternal space may alternatively be referred to by the terms "retrosternal space" or "mediastinum" or "infrasternal" as is known to those skilled in the art and includes the anterior mediastinum 3. The sub-sternal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62. In other words, the distal portion of lead 16 may be implanted in the region around the outer surface of heart 6, but not attached to heart 6.

Figure 2:
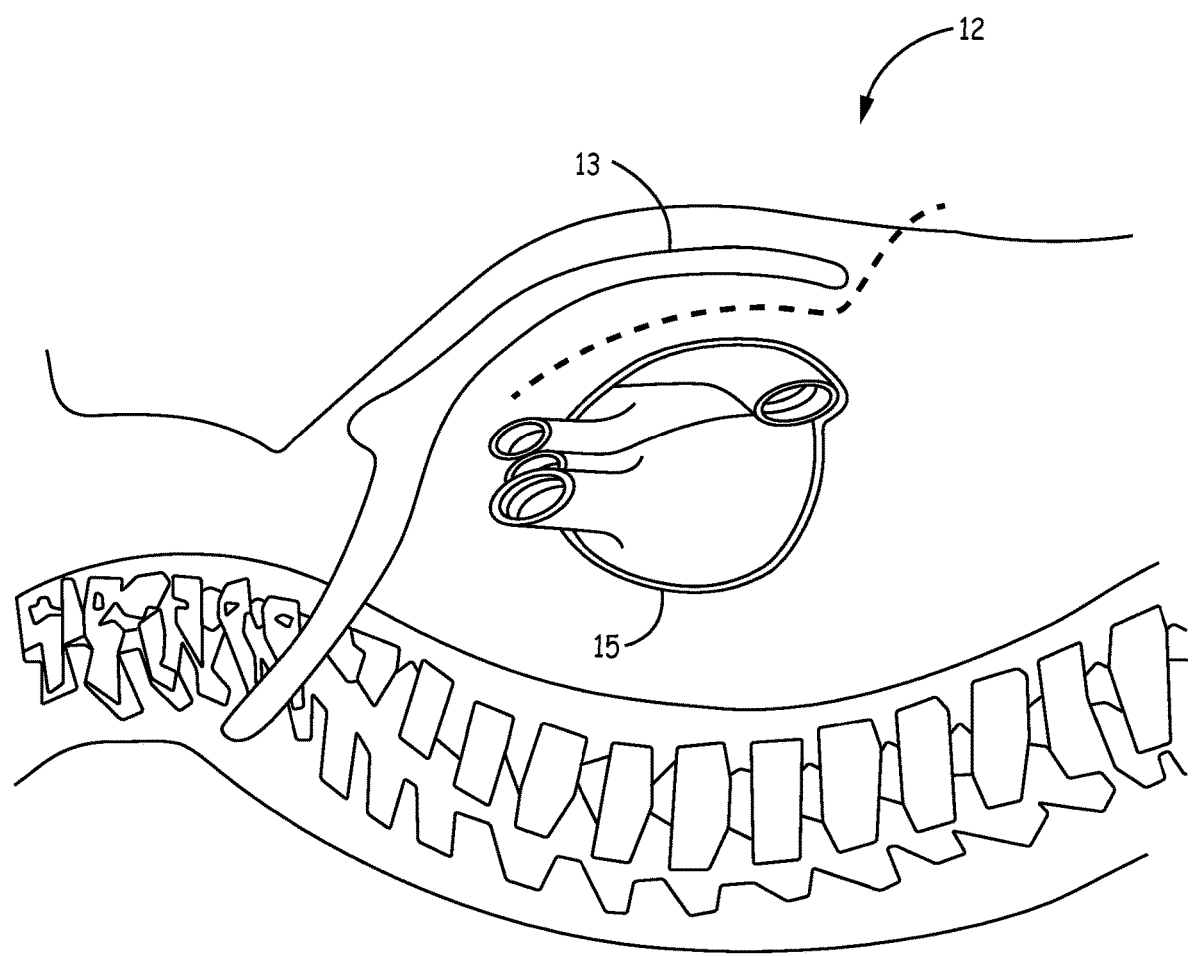
FIG. 2 is a schematic depicting an exemplary tunneling path for forming a tunnel within a sub-sternal space to which an implantable medical electrical lead may be deployed for implant.
Figure 3:
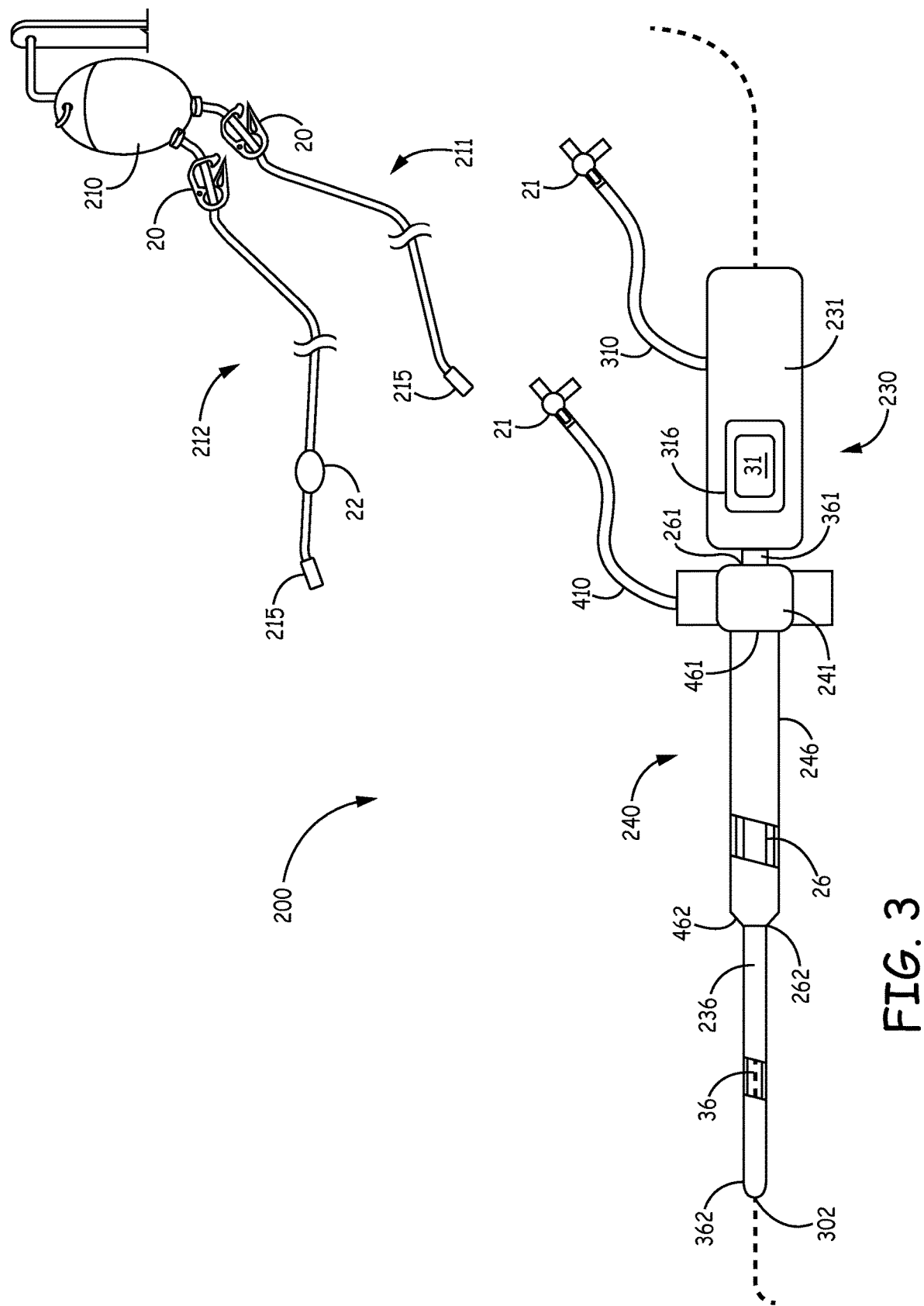
FIG. 3 is a plan view that includes partial cross-sections of a system for deploying a medical electrical lead, for example, to the sub-sternal space of FIG. 2, according to some embodiments.
Figure 4:
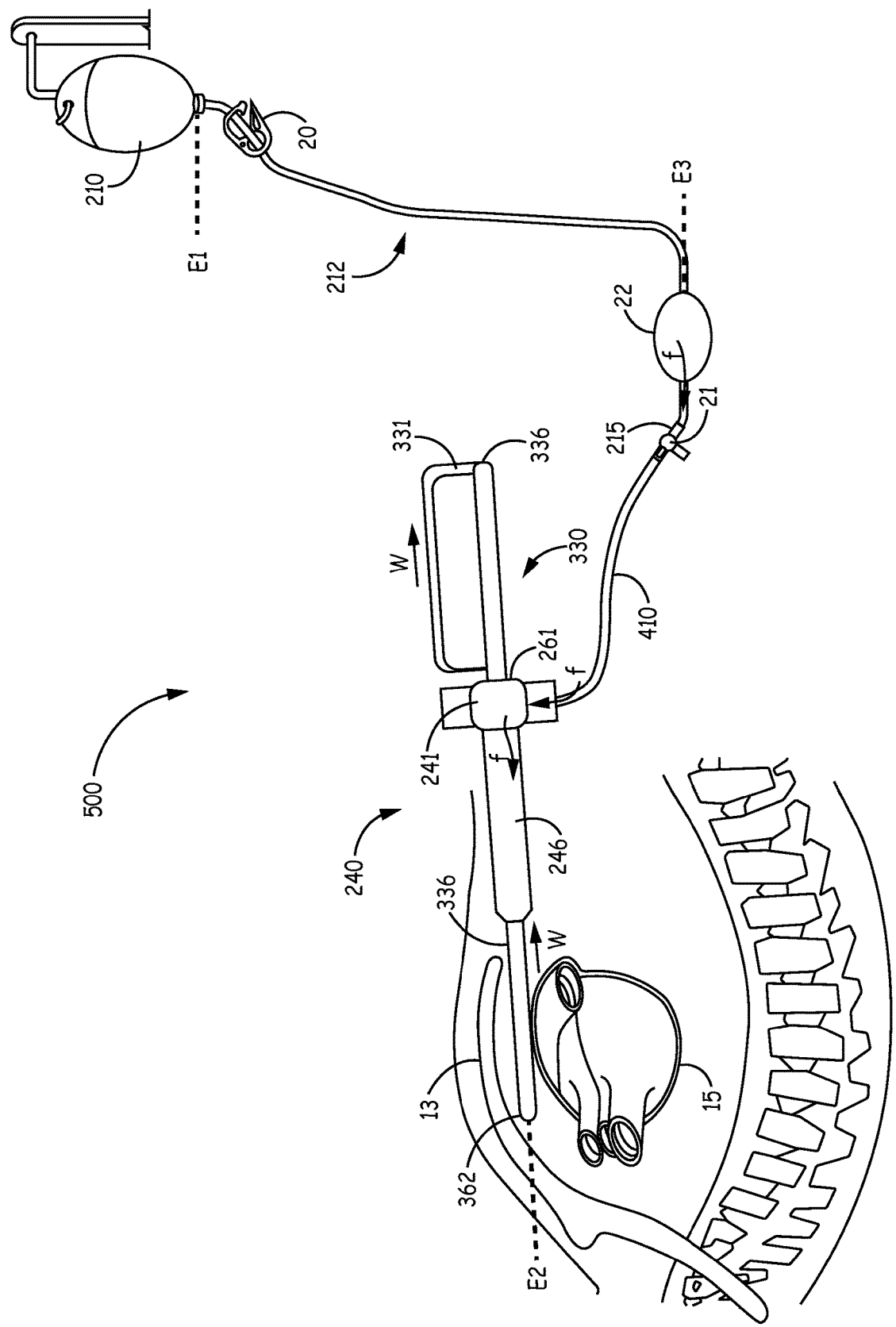
FIG. 4 is a plan view of another system, according some alternate embodiments.

FIG. 2 shows an exemplary sub-sternal path (dashed lines) along which an operator may insert a shaft of a tunneling tool, that is, any tool suited to create an elongate space or tunnel within a body of a patient to receive deployment of an implantable medical electrical lead therein. When inserting the tunneling tool along the path of FIG. 2 (dashed line) and through the above-described sub-sternal tissue, care must be taken by the operator not to perforate through sub-sternal structures or into the chest cavity, which could compromise the pleura 39 of the lungs or the heart 6. The operator must also take care not to draw air into the sub-sternal space when withdrawing the tunneling tool therefrom, to make way for insertion of the medical electrical lead therein, since drawn in air may form pockets around electrodes of the subsequently inserted lead, thereby impacting initial electrode function, for example, by increasing cardiac pacing thresholds and/or impedance and/or cardiac defibrillation thresholds. FIGS. 3 and 4 are plan views of a system 200 and a system 500, respectively, each for deploying a medical electrical lead, according to some alternate embodiments that address these difficulties.

FIG. 3 illustrates system 200 including a tunneling tool 230, which has an elongate and relatively rigid shaft 236. Shaft 236 may be formed from any of a number of medical grade materials, including but not limited to stainless steel. In an exemplary embodiment, shaft has a diameter of approximately 3 millimeters and a length of approximately 30 centimeters, however, shaft 236 may have a smaller or greater diameter and length. Shaft 236, which has a constant stiffness along an entire length thereof, is shown including a blunt distal tip 362 and a lumen 36 extending from a proximal opening thereof (not shown) to a distal opening 302 thereof at distal tip 362. A handle 231 of tunneling tool 230, to which a proximal end 361 of shaft 236 is secured, is shown including a port 310, which is in fluid communication with shaft lumen 36, and a pressure sensor assembly 316 mounted therein. FIG. 3 further illustrates system 200 including a fluid supply assembly, which includes a fluid reservoir 210, for example, filled with a saline solution, and at least one passageway 211 coupled thereto. Passageway 211 is configured for coupling to port 310 of tunneling tool 230, for example, via connection of a luer fitting 215 thereof to a stopcock type valve connector 21 of port 310. Fluid from reservoir 210 flows through passageway 211, for example, being driven by a pressure head created by an elevation of reservoir 210, and is shown being flow-controlled by a clip-type flow restrictor 20.

According to the illustrated embodiment, port 310 of tunneling tool 230 is in fluid communication with lumen 36 of tunneling tool 230, as is a pressure transducer/gauge (not shown) of pressure sensor assembly 316. Thus, when flow-controlled passageway 211 is coupled to port 310, fluid may flow from reservoir 210 and through tunneling tool lumen 36 while a change in pressure of the flow is measured by the pressure transducer. FIG. 3 illustrates pressure sensor assembly 316 including a display 31 conveniently located on handle 231 so that, as the operator is using tunneling tool 230 to create a tunnel within the sub-sternal space, for example, by inserting shaft 236 along the path of FIG. 2, the operator can view display 31 to monitor pressure changes in the flow of fluid through shaft lumen 36, as influenced by the insertion of shaft 236 along the path, thereby gaining some feedback concerning whether or not distal tip 362 has perforated into another bodily cavity. According to some exemplary embodiments, the pressure transducer/gauge may be specified in accordance with the following:

Continuous Flow Rate: 3 cc/hr (±1 cc/hr) or 30 cc/hr (±10 cc/hr) at 300 mmHg
Operating Pressure Range: −50 to +300 mmHg
Sensitivity: 5 μV/V/mmHg, ±2% (typically <±1%)
Overpressure Protection: −400 to +4000 mmHg
Operating Temperature: 15° C. to 40° C.
Operating Life: >500 hours
Storage Temperature: −25° C. to +65° C.
Natural Frequency: >200 Hz in saline However, the pressure transducer/gauge may have other specifications without departing from the scope of this disclosure.

In some embodiments, lumen 36 of tunneling tool 230 may be used to receive a guide wire (dashed lines of FIG. 3) in sliding engagement therewith. In these embodiments, according to some methods, an operator can advance an atraumatic distal end of the guide wire ahead of distal tip 236 to help estimate whether or not a perforation is likely with further advancement of relatively rigid shaft 236.

With further reference to FIG. 3, system 200 further includes an introducer 240, wherein a lumen 26 defined by a tubular member 246 of introducer 240, is snuggly fitted around tunneling tool shaft 236 for sliding engagement therewith. A wall of tubular member 246 is relatively flexible, for example, being formed from polytetrafluoroethylene (PTFE), Fluorinated ethylene propylene (FEP), or polyether block amide (PEBAX®). A proximal end 461 of tubular member 246 is shown being attached to a proximal terminal hub 241 of introducer 240, which may be formed in part by a relatively rigid plastic, such as PEBAX®; a proximal opening 261 of lumen 26 is formed by hub 241, for example, being defined by a seal within hub 241. The seal within hub 241 may be any suitable type, for example, formed from an elastomeric material such as silicone rubber, which allows passage of an elongate body therethrough, such as tunneling tool shaft 236 or a medical electrical lead, while forming a seal thereabout, one example of which is a slit valve. Lumen 26 extends from proximal opening 261 to a distal opening 262 thereof, at a tapered distal end 462 of tubular member 246. According to the illustrated embodiment, distal end 462 of tubular member 246 tapers down to a diameter that approaches an outer diameter of tunneling tool shaft 236 so that the operator can advance, with relative ease, introducer 240 over shaft 236 and into the sub-sternal space in which shaft 236 is inserted. Once within the space, and after the operator withdraws tunneling tool shaft 236, introducer lumen 26 can serve as a conduit through which the operator may deploy an implantable medical electrical lead to the space, after which the operator may remove introducer 240 from around the deployed lead, for example, by splitting or slitting introducer 240, according to methods known in the art. According to some embodiments, the fluid flow through lumen 36 of tunneling tool shaft 236, via the above-described coupling of port 310 to flow-controlled passageway 211, continues while shaft 236 is withdrawn, and is sufficient to fill the void left behind by shaft 236, so that a vacuum does not draw air into the space. But, in some embodiments, a port 410 of introducer hub 241, which is in fluid communication with introducer lumen 26, can be coupled to another flow-controlled passageway 212 of the fluid supply assembly, for example, via connector 215, as shown in FIG. 4, so that a flow of fluid from reservoir 210 through lumen 26 can supplement that through tunneling tool lumen 36 to fill the void left by the withdrawn tunneling tool shaft 236.

FIG. 4 illustrates system 500 including a standard tunneling tool 330 (e.g., Medtronic® Model 6996T tunneling tool), which is shown engaged within introducer lumen 26 and inserted into the patient's body to create a tunnel within the sub-sternal space, for example, along the path of FIG. 2. A shaft 336 of tunneling tool 330 includes a blunt distal tip 362, like shaft 236 of tool 230, but does not include a lumen; however, according to some alternate embodiments, the above-described tunneling tool 230 may be employed in lieu of tool 330, with flow-controlled passageway 211 coupled to port 310 thereof (FIG. 3). FIG. 4 further illustrates fluid reservoir 210 located at a first elevation E1 and a working plane of tunneling tool 330 located at a second elevation E2, which is lower than first elevation E1. Thus, flow-controlled passageway 212, by means of the pressure head created by elevation E1, provides a steady flow of fluid through introducer lumen 26 via a coupling thereof to port 410 of introducer hub 214 (as would passageway 211 through lumen 36 of tunneling tool 230 via port 310, in alternate embodiments). Port 410, like port 310 of tunneling tool 230, is shown including valve connector 21, to which connector 215 of passageway 212 is coupled. The rate of flow from reservoir 210 and through passageway 212, for example, being controlled by clip 20, is limited to prevent flooding of the path of tunneling tool shaft 336, but, when shaft 336 is withdrawn, this rate of flow may not be rapid enough to fill the vacuum and prevent air from being sucked into the space. Thus, with further reference to FIGS. 3 and 4, flow-controlled passageway 212 includes a compliant chamber 22 to retain a reserve of fluid that flows therethrough from reservoir 210, for example, to function as an accumulator, which is then available to provide more rapid flow, per arrow f, in response to the vacuum created when the operator withdraws tunneling tool 330, per arrow W, for example, by pulling on a proximal portion of shaft 336 that is formed into a handle 331. According to some methods, as shown in FIG. 4, chamber 22 is located at an elevation E3 which is lower than elevation E2, which may be necessary to prevent the reserve of fluid from compliant chamber 22 from draining into the path of tunneling tool shaft 336 before tunneling tool 330 is withdrawn.

Figure 5:
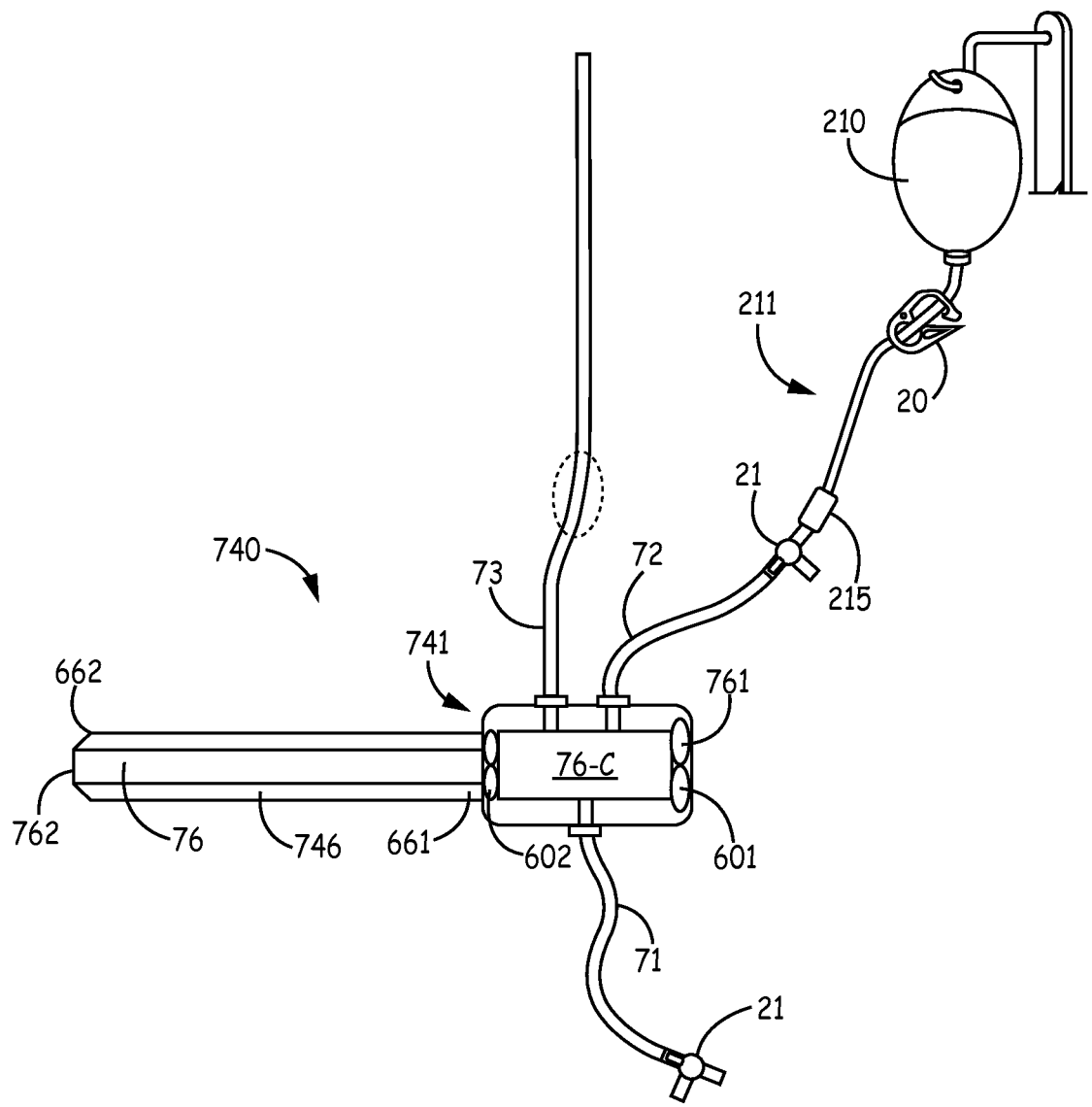
FIG. 5 is a longitudinal cross-section view of an introducer which may be employed by a system, according to some additional embodiments.

FIG. 5 is a longitudinal cross-section view of an introducer 740 which may be employed by a system, according to some additional embodiments, being used in conjunction with either of the above-described tunneling tools 230, 330, or with a standard dilator tool that an operator may use as a tunneling tool. FIG. 5 illustrates introducer 740 including a tubular member 746 and a proximal terminal hub 741 to which a proximal end 661 of tubular member 746 is attached, wherein tubular member 746 defines a lumen 76, and hub 741 includes a proximal seal 601 that defines a proximal opening 761 of lumen 76. Lumen 76 extends from proximal opening 761 to a distal opening 762 thereof, at a tapered distal end 662 of member 746, and includes a chamber 76-C located within hub 741, between proximal seal 601 and a distal seal 602 thereof. Each of seals 601, 602, like the seal of hub 241, described above, may be formed from an elastomeric material and allow passage of an elongate body therethrough while forming a seal thereabout. FIG. 5 further illustrates hub 741 including first, second and third ports 71, 72, 73, all in fluid communication with chamber 76-C, wherein first port 71 may be employed for flushing of chamber 76-C, by opening valve connector 21 thereof, second port 72 is coupled to flow-controlled passageway 211 (e.g., by valve connector 21) so that chamber 76-C may be filled with fluid from reservoir 210, and third port 73 accommodates a standing column of fluid from chamber 76-C, which can act as an accumulator and is open to atmospheric pressure to allow air bubbles to escape. According to the illustrated embodiment, proximal and distal seals 601, 602 function to retain fluid within chamber 76-C and within the standing column of fluid in third port 73, so that the fluid-filled chamber 76-C can prevent air from entering lumen 76 when tubular member 746 is inserted within the sub-sternal space, and when tunneling tool shaft 236/336 is withdrawn out from lumen 76 through proximal opening 761, and when another tool or a lead is inserted into lumen 76 via proximal opening 761 for deployment into the sub-sternal space. In some embodiments, port 73 includes a compliant section (shown with dotted lines), through which the standing column of fluid extends, that can enhance an accumulator function of port 73. Furthermore, hub 741 and tubular member 746 of introducer 740 may be configured to split apart for the removal of introducer 740 from around the deployed lead.

Finally, another difficulty that may be encountered, when employing tunneling procedures to deploy implantable medical electrical leads, is the potential of infecting the sub-sternal space. Thus, according to some embodiments and methods, a saline solution that fills fluid reservoir 210 may be mixed with an antibiotic agent (e.g., Meropenem, Ceftriaxone, Cefazoline, Vancomycin, Clindamycin, Neomycin, Cephalexin, or Levofloxacin Quinolone) to fight infection. Thus, while the operator is inserting tunneling tool shaft 236/336 into a patient's body, for example, along the path of FIG. 1, a flow of the antibiotic laced saline solution may be delivered into the space formed by shaft 236/336, either through lumen 36 of shaft 236 and/or through lumen 26/76 of introducer 240/740.

In the foregoing detailed description, the invention has been described with reference to specific embodiments. However, it may be appreciated that various modifications and changes can be made without departing from the scope of the invention as set forth in the appended claims. For example, the delivery systems and techniques of this disclosure may be used to implant medical electrical leads in subcutaneous paths above the ribcage and/or sternum.

The invention claimed is:

1. A system comprising:
a tunneling tool including an elongate and relatively rigid shaft, a handle, and a pressure sensor assembly mounted in the handle, the shaft having a constant stiffness along an entire length thereof, the shaft including a proximal end secured to the handle, a blunt distal tip, and a lumen extending from a proximal opening thereof, at the proximal end of the shaft, to a distal opening thereof, at the distal tip of the shaft, the handle including a port in fluid communication with the lumen, and the pressure sensor assembly including a pressure transducer in fluid communication with the lumen and a display coupled to the transducer;
an introducer including a tubular member and a proximal terminal hub, the tubular member including a proximal end attached to the hub and a tapered distal end, and the tubular member defining a lumen, the lumen of the introducer extending from a proximal opening thereof, formed by the hub, to a distal opening thereof, at the tapered distal end of the tubular member, the lumen of the introducer being snuggly fitted around the shaft of the tunneling tool for sliding engagement therewith, and the lumen of the introducer being sized for sliding engagement of an implantable lead therein, after the shaft of the tunneling tool is withdrawn from engagement therewith; and
a fluid supply assembly including a fluid reservoir, at least one flow-controlled passageway coupled to the reservoir to accommodate a flow of fluid from the reservoir therethrough, and one of the at least one flow-controlled passageway, being configured for coupling to the port of the handle of the tunneling tool;
wherein, when a first passageway of the at least one flow-controlled passageway of the fluid supply assembly is coupled to the port of the handle of the tunneling tool, fluid from the reservoir flows through the first passageway and through the lumen of the tunneling tool, and a change in a pressure of the flow, as measured by the pressure transducer of the pressure sensor assembly, is presented on the display of the pressure sensor assembly, and
wherein:
the hub of the introducer includes a seal defining the proximal opening of the lumen of the introducer, and a port in fluid communication with the lumen of the introducer;
the at least one flow-controlled passageway of the fluid supply assembly includes a second passageway coupled to the fluid reservoir for a flow of fluid from the reservoir in parallel with the fluid flow through the first passageway, the second passageway being configured for coupling to the port of the hub of the introducer;
the second passageway of the at least one flow-controlled passageway of the fluid supply assembly includes a compliant chamber for retaining a reserve of fluid that flows therethrough; and
when the tunneling tool has created a tunnel within a sub-sternal space in a body of a patient, and when the introducer has been slid thereover into the space, and when the second passageway of the at least one flow-controlled passageway of the fluid supply assembly is coupled to the port of the introducer, fluid in the compliant chamber is drawn therefrom and into the lumen of the introducer as the tunneling tool is withdrawn from engagement therewith, through the proximal opening of the lumen of the introducer.

2. The system of claim 1, further comprising a guide wire, the lumen of the tunneling tool being sized for sliding engagement of the guide wire therein.

3. The system of claim 1, wherein the fluid in the fluid reservoir of the fluid supply assembly comprises a saline solution mixed with an antibiotic agent.

4. The system of claim 1, wherein the display is located on the handle of the tunneling tool.

5. The system of claim 1, wherein the flow of the fluid from the reservoir through the first passageway and through the lumen of the tunneling tool is configured to be driven by a pressure head created by an elevation of the reservoir relative to the tunneling tool.

6. The system of claim 1, wherein the change in a pressure of the flow of fluid is influenced by the insertion of the shaft of the tunneling tool in a sub-sternal space of a body of a patient.

7. A system comprising:
a tool including an elongate and relatively rigid shaft for tunneling, the shaft including a blunt distal tip and having a constant stiffness along an entire length thereof;
an introducer including a tubular member and a proximal terminal hub, the hub including a distal seal, a proximal seal, and first, second, and third ports, the tubular member including a proximal end attached to the hub and a tapered distal end, and the tubular member defining a lumen, the lumen extending from a proximal opening thereof, defined by the proximal seal of the hub, to a distal opening thereof, at the tapered distal end of the tubular member, the lumen being snuggly fitted around the shaft of the tool for sliding engagement therewith, the lumen being sized for sliding engagement of an implantable lead therein, after the shaft of the tool is withdrawn from engagement therewith, and the lumen including a chamber located within the hub and between the proximal and distal seals, the first port being in fluid communication with the chamber and including a valve connector, the second port being in fluid communication with the chamber, and the third port being in fluid communication with the chamber and configured to accommodate a standing column of fluid from the chamber, the standing column being open to atmospheric pressure; and
a fluid supply assembly including a fluid reservoir, a flow-controlled passageway coupled to the reservoir to accommodate a flow of fluid from the reservoir therethrough, the flow-controlled passageway being configured for coupling to the second port of the hub of the introducer, so that, when coupled, the flow-controlled passageway delivers fluid from the reservoir to fill the chamber of the introducer lumen and to create the standing column of fluid in the third port of the hub of the introducer; and
wherein, when the tool and the introducer have been inserted into a sub-sternal space in a body of a patient, and when the flow-controlled passageway of the fluid supply assembly is coupled to the second port of the introducer, fluid from the chamber of the introducer lumen is drawn distally through the distal seal of the introducer hub as the tool is withdrawn from engagement with the introducer, through the proximal opening of the lumen of the introducer.

8. The system of claim 7, wherein the third port of the hub of the introducer includes a compliant section through which the standing column of fluid extends.

9. The system of claim 7, wherein the fluid in the fluid reservoir of the fluid supply assembly comprises a saline solution mixed with an antibiotic agent.

10. The system of claim 7, wherein the standing column acts as an accumulator.

11. The system of claim 7, wherein the standing column allows air bubbles in the chamber to escape the chamber via the third port.

12. The system of claim 7, wherein the fluid is configured to flow from the standing column to the chamber via the third port.

13. The system of claim 7, wherein the chamber is configured to be flushed via the first port when the valve connector is in an open position.

14. The system of claim 7, wherein the fluid from the reservoir is configured to flow into the chamber via the flow-controlled passageway through the second port when the flow-controlled passageway is coupled to the second port.

15. A system comprising:
a tunneling tool including an elongate and relatively rigid shaft, a handle, and a pressure sensor assembly mounted in the handle, the shaft having a constant stiffness along an entire length thereof, the shaft including a proximal end secured to the handle, a blunt distal tip, and a lumen extending from a proximal opening thereof, at the proximal end of the shaft, to a distal opening thereof, at the distal tip of the shaft, the handle including a port in fluid communication with the lumen, and the pressure sensor assembly including a pressure transducer in fluid communication with the lumen and a display coupled to the transducer;
an introducer including a tubular member and a proximal terminal hub, the tubular member including a proximal end attached to the hub and a tapered distal end, and the tubular member defining a lumen, the lumen of the introducer extending from a proximal opening thereof, formed by the hub, to a distal opening thereof, at the tapered distal end of the tubular member, the lumen of the introducer being snuggly fitted around the shaft of the tunneling tool for sliding engagement therewith, and the lumen of the introducer being sized for sliding engagement of an implantable lead therein, after the shaft of the tunneling tool is withdrawn from engagement therewith; and
a fluid supply assembly including a fluid reservoir, at least one flow-controlled passageway coupled to the reservoir to accommodate a flow of fluid from the reservoir therethrough, and one of the at least one flow-controlled passageway, being configured for coupling to the port of the handle of the tunneling tool;
wherein, when a first passageway of the at least one flow-controlled passageway of the fluid supply assembly is coupled to the port of the handle of the tunneling tool, fluid from the reservoir flows through the first passageway and through the lumen of the tunneling tool, and a change in a pressure of the flow, as measured by the pressure transducer of the pressure sensor assembly, is presented on the display of the pressure sensor assembly, and
wherein:
the lumen of the introducer further includes a chamber;
the hub of the introducer includes a distal seal, a proximal seal, and first, second, and third ports, the chamber of the lumen of the introducer being located between the proximal and distal seals, the proximal seal defining the proximal opening of the lumen of the introducer, the first port being in fluid communication with the chamber and including a valve connector, the second port being in fluid communication with the chamber, and the third port being in fluid communication with the chamber and configured to accommodate a standing column of fluid from the chamber, the standing column being open to atmospheric pressure;
the at least one flow-controlled passageway of the fluid supply assembly includes a second passageway, the second passageway being coupled to the fluid reservoir for a flow of fluid from the reservoir in parallel with the fluid flow through the first passageway, and the second passageway being configured for coupling to the second port of the hub of the introducer, so that, when coupled, fluid from the reservoir flows through the second passageway to fill the chamber of the introducer lumen and to create the standing column of fluid in the third port of the hub of the introducer; and when the tunneling tool has created a tunnel within a sub-sternal space in a body of a patient, and when the introducer has been slid thereover into the space, and when the second passageway of the at least one flow-controlled passageway of the fluid supply assembly is coupled to the second port of the introducer, fluid from the chamber of the introducer lumen is drawn distally through the distal seal of the introducer hub as the tunneling tool is withdrawn from engagement with the introducer, through the proximal opening of the lumen of the introducer.

16. The system of claim 15, wherein the third port of the hub of the introducer includes a compliant section through which the standing column of fluid extends.

17. The system of claim 15, further comprising a guide wire, the lumen of the tunneling tool being sized for sliding engagement of the guide wire therein.

18. The system of claim 15, wherein the fluid in the fluid reservoir of the fluid supply assembly comprises a saline solution mixed with an antibiotic agent.

* * * * *